(12) United States Patent
Chen

(10) Patent No.: US 10,188,489 B2
(45) Date of Patent: Jan. 29, 2019

(54) SINUS IMPLANT

(71) Applicant: Star Generation Limited Taiwan Branch, Taipei (TW)

(72) Inventor: Chun-Leon Chen, New Taipei (TW)

(73) Assignee: Star Generation Limited Taiwan Branch, Taipei (TW)

( * ) Notice: Subject to any disclaimer, the term of this patent is extended or adjusted under 35 U.S.C. 154(b) by 29 days.

(21) Appl. No.: 14/254,922

(22) Filed: Apr. 17, 2014

(65) Prior Publication Data

US 2015/0297323 A1    Oct. 22, 2015

(51) Int. Cl.
 *A61C 8/00*    (2006.01)

(52) U.S. Cl.
 CPC .......... *A61C 8/0092* (2013.01); *A61C 8/0068* (2013.01); *A61C 8/0025* (2013.01); *A61C 8/0039* (2013.01)

(58) Field of Classification Search
 CPC ............................ A61C 8/0025; A61C 8/0039
 See application file for complete search history.

(56) References Cited

U.S. PATENT DOCUMENTS

| | | |
|---|---|---|
| 1,698,951 A | 1/1929 | Holmes |
| 3,590,485 A | 7/1971 | Chercheve et al. |
| 4,239,489 A | 12/1980 | Ellman et al. |
| 4,259,072 A | 3/1981 | Hirabayashi et al. |
| 4,293,302 A | 10/1981 | Hassler et al. |
| 4,411,624 A | 10/1983 | Ogino et al. |
| 4,424,037 A | 1/1984 | Ogino et al. |
| 4,446,579 A | 5/1984 | Inamori et al. |
| 4,697,969 A | 10/1987 | Sparkes |
| 4,731,085 A | 3/1988 | Koch |
| 4,871,313 A | 10/1989 | Maillefer |
| 5,033,999 A | 7/1991 | Mersky |
| 5,152,687 A | 10/1992 | Amino |
| 5,174,755 A | 12/1992 | Fukuda |
| 5,316,476 A * | 5/1994 | Krauser .............. A61C 8/0018 433/173 |
| 5,437,551 A | 8/1995 | Chalifoux |

(Continued)

FOREIGN PATENT DOCUMENTS

| | | |
|---|---|---|
| CN | 201727594 U | 2/2011 |
| CN | 102920517 A | 2/2013 |

(Continued)

*Primary Examiner* — Ralph Lewis
(74) *Attorney, Agent, or Firm* — Rabin & Berdo, P.C.

(57) ABSTRACT

A sinus implant includes an implant body having a mounting hole axially defined there through; a plurality of positioning threads that are provided in a periphery of the implant body, that extend spirally upwardly around the periphery of the implant body, and that have a width that gradually decreases in a direction from a bottom end of the implant body toward an opposing top end of the implant body; a pushing tip that protrudes from a top end of the sinus implant, that has a diameter that is reduced compared to that of the implant body, and that includes a flat end face having defined therein a recess space; and at least one spiral groove that extends around the periphery of the implant body across the plurality of positioning threads, that reaches the periphery of the pushing tip, and that intersects with and communicates with the recess space.

9 Claims, 8 Drawing Sheets

(56) References Cited

U.S. PATENT DOCUMENTS

| | | | |
|---|---|---|---|
| 5,571,017 A * | 11/1996 | Niznick | A61C 8/0022 433/173 |
| 5,620,323 A | 4/1997 | Bressman et al. | |
| 5,702,346 A | 12/1997 | Lazzara et al. | |
| 5,702,445 A | 12/1997 | Branemark | |
| 5,871,356 A * | 2/1999 | Guedj | A61C 8/0022 433/165 |
| 5,871,359 A | 2/1999 | Billet et al. | |
| 5,897,319 A | 4/1999 | Wagner et al. | |
| 6,068,632 A | 5/2000 | Carchidi et al. | |
| 6,099,312 A | 8/2000 | Alvaro | |
| 6,102,702 A | 8/2000 | Folsom, Jr. et al. | |
| 6,102,703 A | 8/2000 | Day | |
| 6,217,331 B1 | 4/2001 | Rogers et al. | |
| 6,234,797 B1 | 5/2001 | Ura | |
| 6,382,976 B1 * | 5/2002 | Wagner | A61C 8/0022 433/174 |
| 6,402,757 B1 | 6/2002 | Moore, III et al. | |
| 6,604,945 B1 | 8/2003 | Jones | |
| 7,338,286 B2 | 3/2008 | Porter et al. | |
| 7,396,231 B2 | 7/2008 | Niznick | |
| 7,517,218 B2 | 4/2009 | Hansson | |
| 7,677,891 B2 | 3/2010 | Niznick | |
| 7,708,738 B2 | 5/2010 | Fourcault et al. | |
| 7,785,107 B2 | 8/2010 | Niznick | |
| 7,845,945 B2 * | 12/2010 | Canter | A61C 8/0018 433/173 |
| 7,883,336 B2 | 2/2011 | Hansson | |
| 8,052,422 B2 * | 11/2011 | Hung | A61C 8/0018 433/174 |
| 8,721,334 B2 * | 5/2014 | Better | A61C 8/0018 433/165 |
| 8,814,567 B2 | 8/2014 | Zhang et al. | |
| 8,870,573 B2 * | 10/2014 | Hung | A61C 8/0039 433/174 |
| 8,986,007 B2 | 3/2015 | Chen | |
| 2002/0006595 A1 | 1/2002 | Voudouris | |
| 2002/0182559 A1 | 12/2002 | Kamisugi | |
| 2003/0104338 A1 | 6/2003 | Cottrell | |
| 2004/0170947 A1 | 9/2004 | Milne | |
| 2004/0185421 A1 | 9/2004 | Schulter et al. | |
| 2004/0219488 A1 | 11/2004 | Choi et al. | |
| 2005/0136378 A1 | 6/2005 | Ennajimi | |
| 2005/0196723 A1 | 9/2005 | Monkmeyer | |
| 2005/0282111 A1 | 12/2005 | Ito | |
| 2006/0172258 A1 | 8/2006 | Niznick | |
| 2006/0199149 A1 | 9/2006 | Niznick | |
| 2006/0199150 A1 | 9/2006 | Niznick | |
| 2006/0246398 A1 | 11/2006 | Groff et al. | |
| 2006/0246399 A1 | 11/2006 | Ehrl | |
| 2007/0134615 A1 | 6/2007 | Lovely | |
| 2007/0141535 A1 | 6/2007 | Baldissara | |
| 2007/0275347 A1 | 11/2007 | Gruber | |
| 2007/0298379 A1 | 12/2007 | D'Alise | |
| 2008/0003540 A1 | 1/2008 | Khawaled et al. | |
| 2008/0020348 A1 | 1/2008 | Hansson | |
| 2008/0050699 A1 | 2/2008 | Zhang et al. | |
| 2008/0081316 A1 | 4/2008 | Chung | |
| 2008/0145819 A1 | 6/2008 | Boettcher | |
| 2008/0233539 A1 | 9/2008 | Rossler et al. | |
| 2008/0261175 A1 | 10/2008 | Hurson | |
| 2008/0280255 A1 | 11/2008 | D'Alise | |
| 2009/0061387 A1 | 3/2009 | Lomicka et al. | |
| 2009/0061389 A1 | 3/2009 | Lomicka et al. | |
| 2009/0220914 A1 | 9/2009 | Gershenzon | |
| 2010/0009316 A1 | 1/2010 | Hurson | |
| 2010/0015571 A1 | 1/2010 | Al-Attar | |
| 2010/0046697 A1 | 2/2010 | Laster et al. | |
| 2010/0261142 A1 * | 10/2010 | Metz-Stavenhagen | A61C 8/0039 433/174 |
| 2011/0033826 A1 | 2/2011 | Chen | |
| 2012/0046697 A1 * | 2/2012 | Laster | A61B 17/863 606/301 |
| 2012/0077151 A1 | 3/2012 | Nary Fiiho et al. | |
| 2012/0189984 A1 * | 7/2012 | Holmes | A61C 8/0039 433/174 |
| 2013/0045462 A1 * | 2/2013 | Tzeng | A61C 8/0018 433/174 |
| 2014/0087331 A1 | 3/2014 | Hildmann et al. | |
| 2014/0227662 A1 | 8/2014 | Di Girolamo et al. | |
| 2015/0086942 A1 | 3/2015 | Hwang | |
| 2015/0147720 A1 * | 5/2015 | Lai | A61C 8/0068 433/173 |
| 2015/0297320 A1 | 10/2015 | Chen | |
| 2015/0297321 A1 | 10/2015 | Chen | |
| 2015/0297323 A1 | 10/2015 | Chen | |

FOREIGN PATENT DOCUMENTS

| | | |
|---|---|---|
| CN | 103371873 A | 10/2013 |
| CN | 204581558 U | 8/2015 |
| CN | 105012025 A | 11/2015 |
| TW | M315571 U | 7/2007 |
| TW | M357962 U | 6/2009 |
| TW | M390130 | 10/2010 |
| TW | M436447 U | 9/2012 |
| TW | M440763 | 11/2012 |
| TW | M500558 U | 5/2015 |
| TW | 201540267 | 11/2015 |
| TW | 201540268 | 11/2015 |
| WO | WO2011055358 A | 5/2011 |

\* cited by examiner

SINUS IMPLANT

BACKGROUND OF THE INVENTION

1. Field of the Invention

The present invention relates to dental implant technology and, more particularly, to a sinus implant that can synchronously push the selected amount of bone growth powder/biomedical filler into the crevice between the sinus floor and the upper gum without damaging or piercing the sinus floor.

2. Description of the Related Art

In a typical dental implant procedure, prior to installation of the dental implant, the dentist will check the conditions of the gum. If the thickness of the cortical bone is insufficient, a bone growth powder/biomedical filler must be supplemented to lift the thickness of the cortical bone. The bone growth powder/biomedical filler filling amount is determined subject to the condition of the patient's dental implant bone area. Thus, a proper implant bone growth powder/biomedical filler thickness can be provided.

As illustrated in FIG. 1, if the thickness of the cortical bone (for example, upper gum) 101 in the implant area around the sinus floor 100 is insufficient and must be lifted, the existing method is to make a drill hole 102 in the cortical bone 101 by osteotomy, then, as shown in FIG. 2, to separate a part of the sinus floor 100 from the cortical bone 101, and, finally, to fill a bone growth powder/biomedical filler 103 into the crevice between the sinus floor 100 and the cortical bone 101 to increase the thickness of the cortical bone 101 and to facilitate the follow-up implant installation procedure. During this bone growth powder/biomedical filler filling procedure, the amount of the applied bone growth powder/biomedical filler is determined subject to the condition of the patient's dental implant bone area. When separating the sinus floor 100 from the cortical bone 101, the dentist must carefully perform the procedure not to pierce the sinus floor, avoiding serious sequelae.

An early bone growth powder/biomedical filler filling tool for dental implant comprises a push pin 104 at the end of a handle for pushing the applied bone growth powder/biomedical filler 103 from the drill hole 102 in the cortical bone 101 into the crevice between the cortical bone 101 and the sinus floor 100. However, this bone growth powder/biomedical filler filling tool is not convenient to operate. It takes much time to fill the applied bone growth powder/biomedical filler into the crevice between the cortical bone and the sinus floor with this design of bone growth powder/biomedical filler filling tool. Operating this bone growth powder/biomedical filler filling tool is a big burden to the dentist and can make the patient feel uncomfortable.

Taiwan Patent M440763 discloses an improved design of bone growth powder/biomedical filler filling tool. This design of bone growth powder/biomedical filler filling tool comprises a bone growth powder/biomedical filler propelling bit that has opposing top end portion and bottom end portion, bone growth powder/biomedical filler transferring grooves spirally extending around the periphery thereof from the top end to the bottom end portions, and bone growth powder/biomedical filler propelling threads extending around the periphery thereof at different elevations for rapidly and uniformly propelling bone growth powder/biomedical filler into the space between the sinus floor and the cortical bone to increase the thickness of the cortical bone in favor of the process of the subsequent tooth implanting, helping the doctor in charge of the operation save operating time and physical strength. This design of bone growth powder/biomedical filler filling tool can help the dentist reduce fatigue and shorten the period the patients feel uncomfortable. However, this design of bone growth powder/biomedical filler filling tool is just a simple tool for filling bone growth powder/biomedical filler prior to the implant installation procedure.

SUMMARY OF THE INVENTION

The present invention has been accomplished under the circumstances in view. It is one object of the present invention to provide a sinus implant that simultaneously pushes the applied bone growth powder/biomedical filler into place without damaging or piercing the sinus floor during installation.

To achieve this and other objects of the present invention, a sinus implant in accordance with the present invention comprises a mounting hole axially defined therein, a plurality of positioning threads spirally upwardly extended around the periphery thereof and gradually reducing in width in direction from a bottom side toward an opposing top side thereof, at least one spiral groove extending around the periphery thereof across the positioning threads, and a pushing tip of reduced diameter located at respective top ends of the positioning threads. The tip comprises a flat end face, and a recess space defined in the flat end face in communication with each spiral groove.

Preferably, the pushing tip further comprises a smoothly arched outer guide edge extending around the border of the flat end face, and a smoothly arched inner guide edge extending around the recess space within the flat end face.

Preferably, the recess space is shaped like a hemisphere.

Further, the positioning threads and each spiral groove can be designed to extend spirally upwardly in the same direction. Alternatively, the positioning threads and each spiral groove can be designed to extend spirally in reversed directions.

DETAILED DESCRIPTION OF THE PREFERRED EMBODIMENTS

Figure 1:
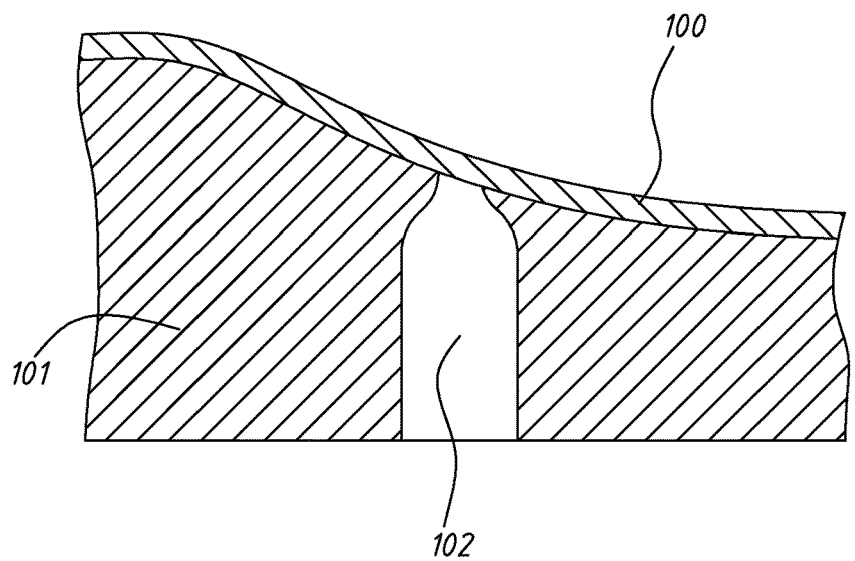
FIG. 1 is a schematic sectional view illustrating a drill hole formed in an upper gum by osteotomy.
Figure 2:
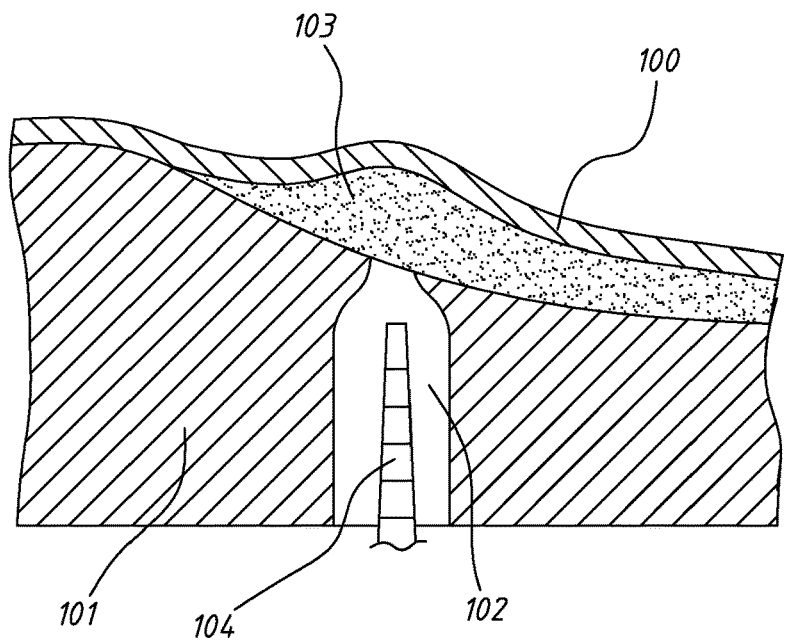
FIG. 2 corresponds to FIG. 1, illustrating a bone growth powder/biomedical filler filled in the crevice between the upper gum and the sinus floor.
Figure 3:
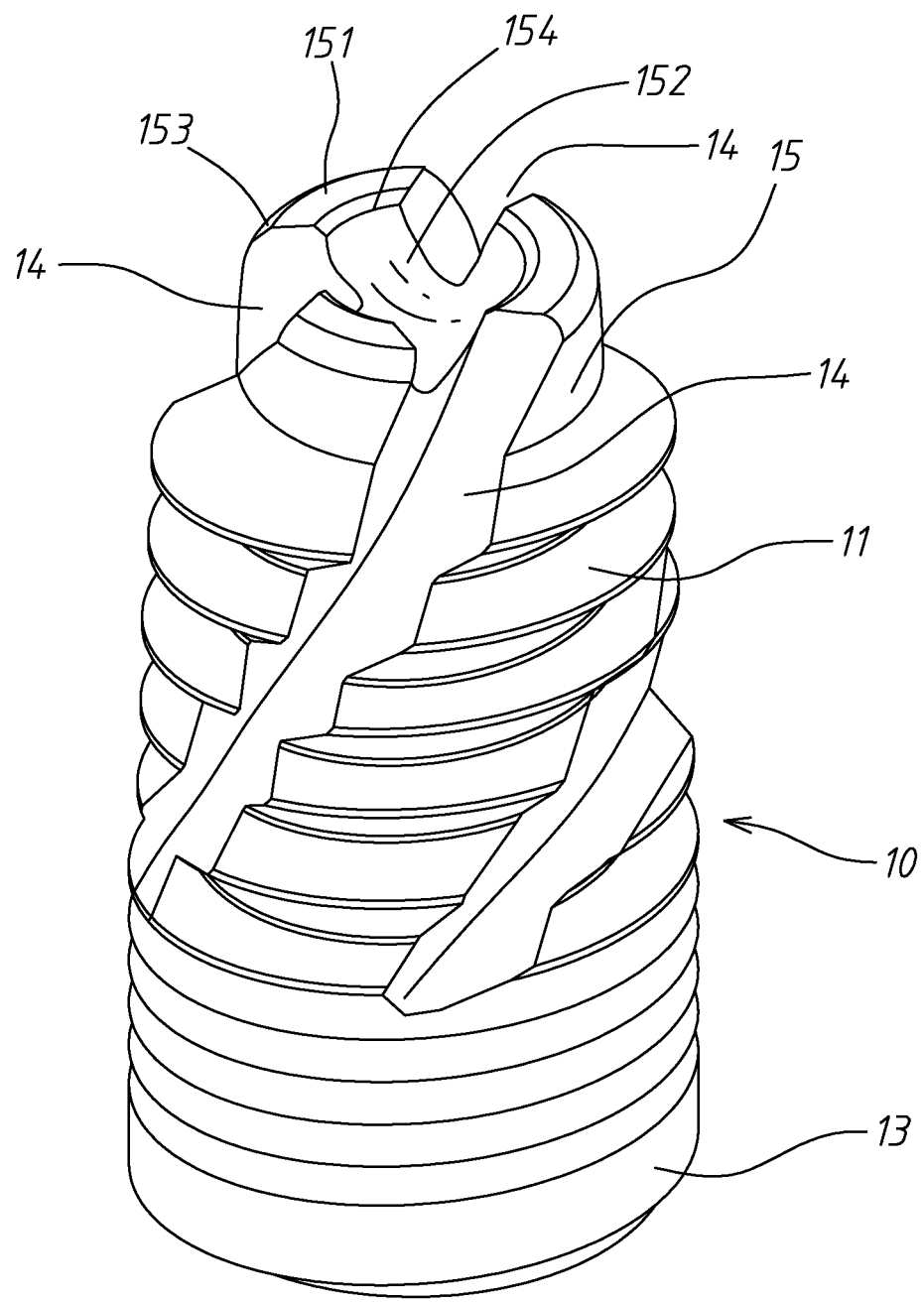
FIG. 3 is an oblique top elevational view of a sinus implant in accordance with a first embodiment of the present invention.
Figure 6:
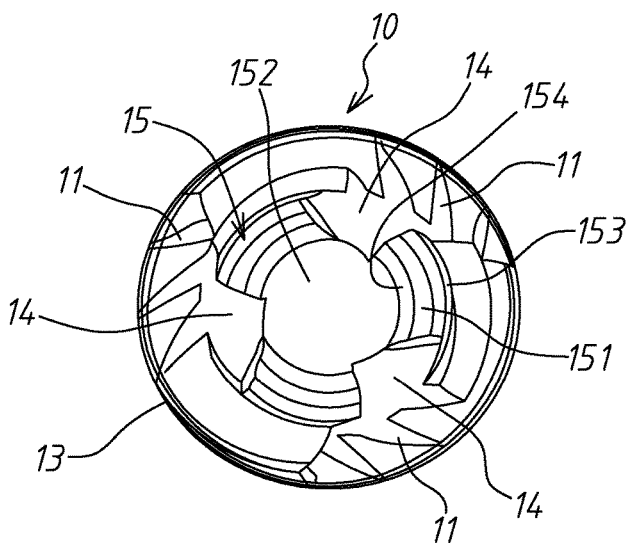
FIG. 6 is a top view of the sinus implant in accordance with the first embodiment of the present invention.
Figure 5:
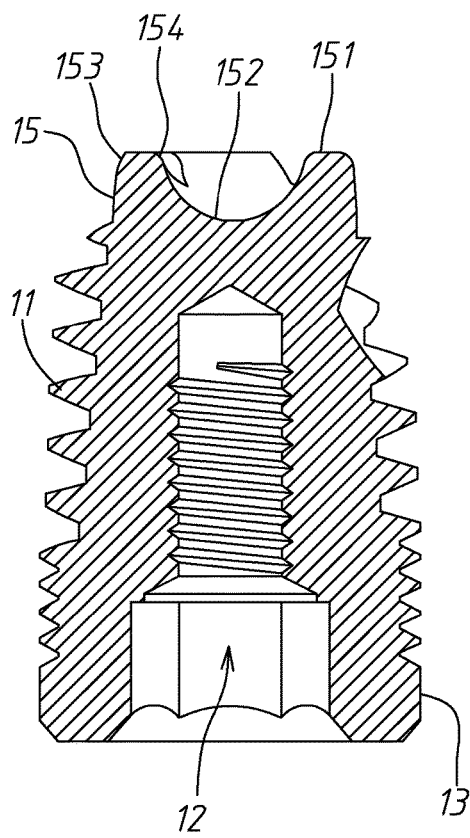
FIG. 5 is a longitudinal sectional view of the sinus implant in accordance with the first embodiment of the present invention.
Figure 4:
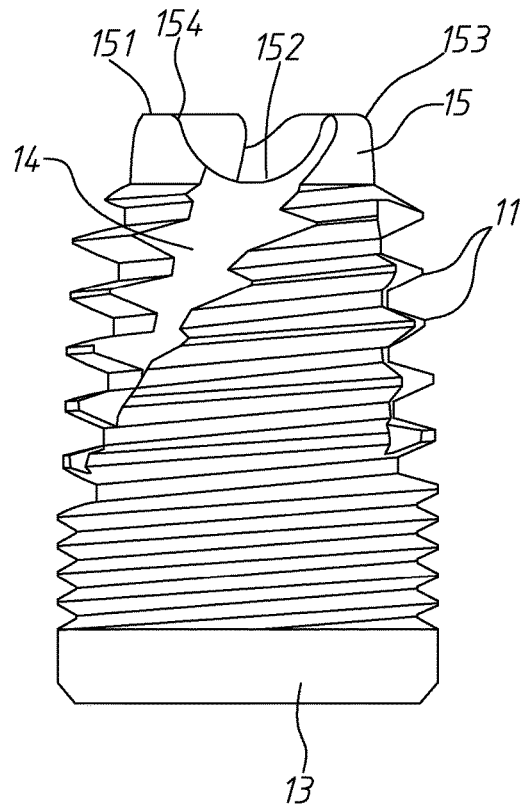
FIG. 4 is a front view of the sinus implant in accordance with the first embodiment of the present invention.

Referring to FIGS. 3-6, a sinus implant 10 in accordance with a first embodiment of the present invention is shown. The sinus implant 10 is prepared from zirconium dioxide and comprises an implant root 13 at a bottom side thereof, a mounting hole 12 axially defined therein and upwardly extended from a bottom edge of the implant root 13 to a predetermined height (see FIG. 5), and a plurality of positioning threads 11 spirally upwardly extended around the periphery thereof and gradually reducing in width in direction from the implant root 13 toward an opposing top side thereof to form a gum-drilling structure. In this embodiment, the positioning threads 11 extend upwardly in a clockwise direction at a fixed pitch. However, this thread extending direction is simply an example but not intended to limit the present invention. Alternatively, the positioning threads 11 can be designed to extend upwardly in a counter-clockwise direction.

The sinus implant 10 further comprises at least one and, for example, three spiral grooves 14 upwardly extending around the periphery thereof across the positioning threads 11 and equally spaced from one another, and a pushing tip 15 of reduced diameter located at the ends of the positioning threads 11 (i.e. at the top side of the sinus implant 10) in axial alignment with the mounting hole 12. The pushing tip 15 defines a flat end face 151, and a recess space 152 in the flat end face 151 in communication with the spiral grooves 14.

In order to facilitate pushing and bone pile and delivery in a safe manner, the border area of the flat end face 151 is preferably smooth. In this embodiment, the flat end face 151 has a smoothly arched outer guide edge 153 around the border thereof, and a smoothly arched inner guide edge 154 in the recess space 152.

Further, in this embodiment, the recess space 152 is shaped like a hemisphere. However, this hemispherical shape is simply an example. The recess space 152 can also be made in any other geometrical shape for accommodation of a bone growth powder/biomedical filler.

Figure 7:
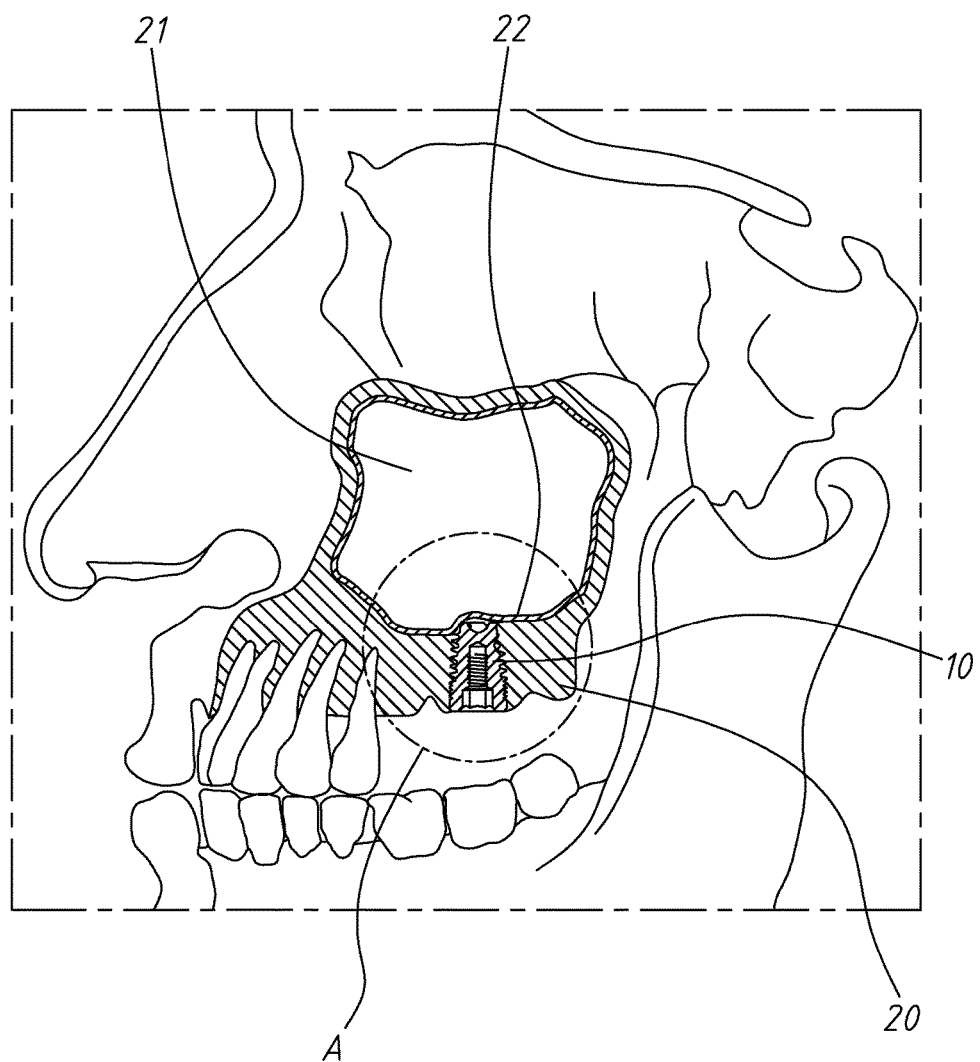
FIG. 7 is a schematic applied view of the first embodiment of the present invention, illustrating the installed position of the sinus implant relative to the upper gum and the sinus floor.
Figure 8:
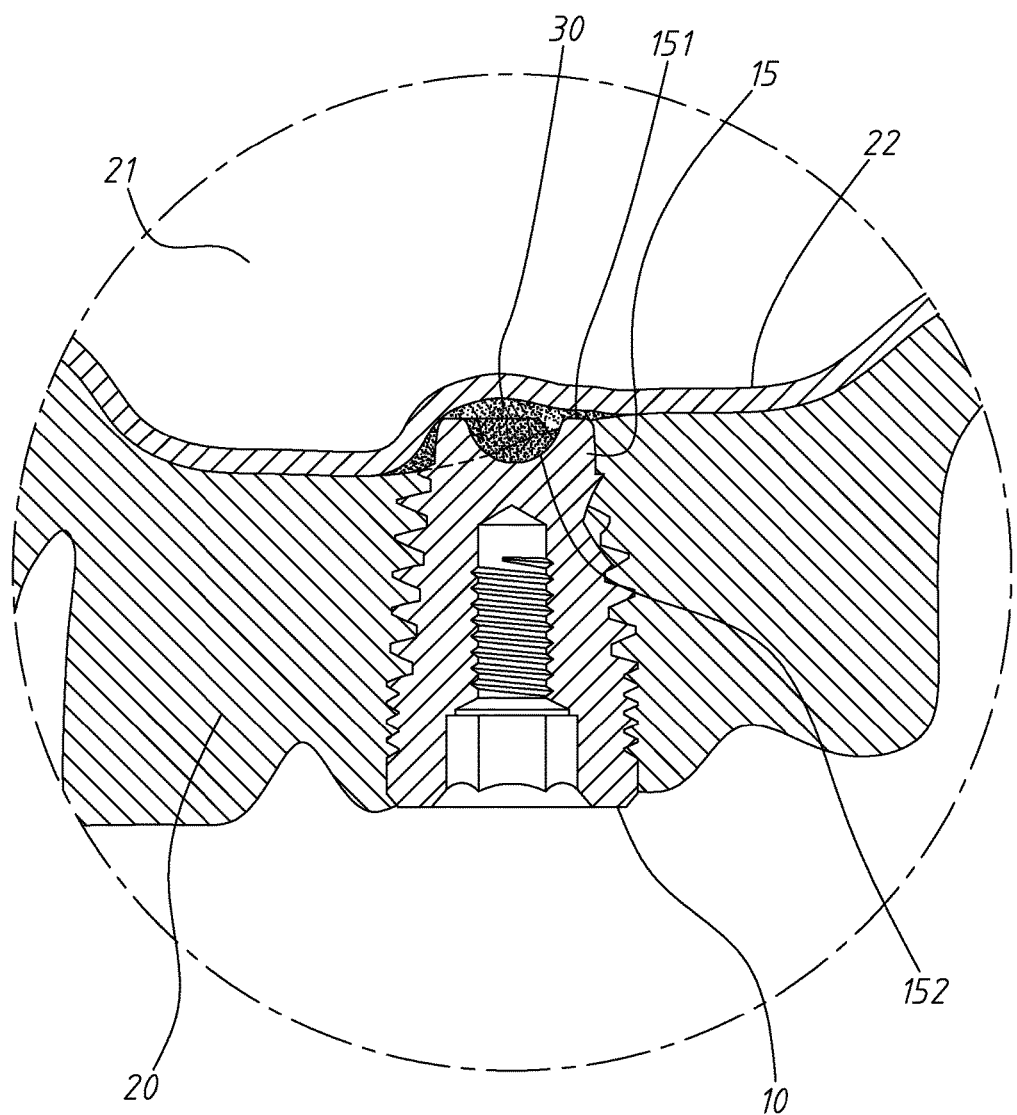
FIG. 8 is an enlarged view of Part A of FIG. 7.

Referring to FIG. 7, in an implant surgery of an upper gum 20, the sinus implant 10 must be driven into the upper gum 20 to push the sinus floor (mucosa) 22 of the sinus 21 for filling a bone growth powder/biomedical filler. During the implant surgery, the dentist fills a bone growth powder/biomedical filler 30 into the drill hole that was made by osteotomy, and then drives the sinus implant 10 into the drill hole. At this time, the design of the spiral grooves 14 of the sinus implant 10 and the design of the recessed space 152 in the flat end face 151 of the pushing tip 15 enable the applied bone growth powder/biomedical filler 30 to be pushed forwards by the sinus implant 10. As the pushing tip 15 gradually pushes open the sinus floor 22, the bone growth powder/biomedical filler 30 is forced to enter the crevice between the sinus floor 22 and the upper gum 20. Thus, the bone growth powder/biomedical filler filling operation is synchronously done when the installation of the sinus implant 10 is completed (see FIG. 8).

Figure 9:
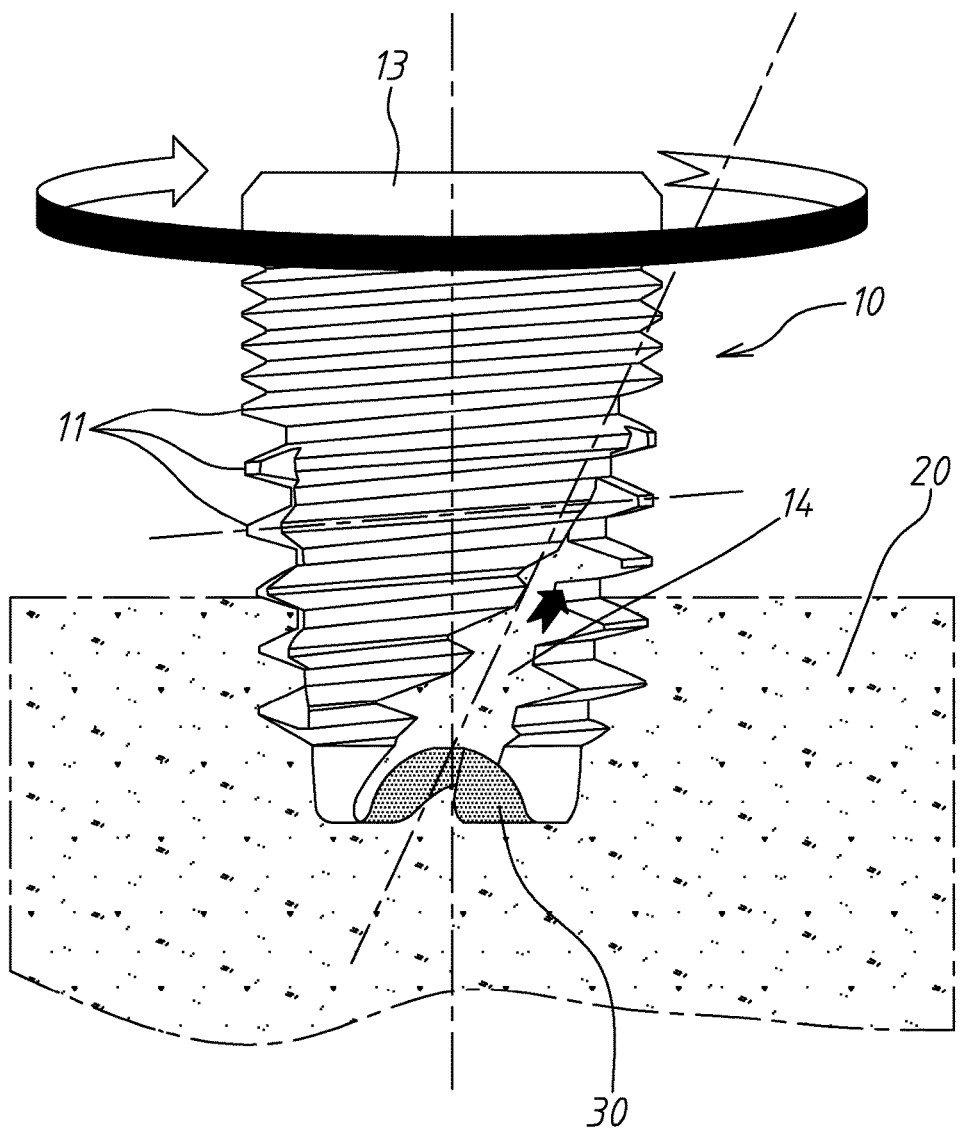
FIG. 9 is a schematic drawing illustrating the action of the installation of the sinus implant of the first embodiment of the present invention in the upper gum.

Referring to FIG. 9, the spiral grooves 14 and the positioning threads 11 of the sinus implant 10 in accordance with the first embodiment of the present invention extend spirally in the same direction. Therefore, when driving the sinus implant 10 into the upper gum 20, each spiral groove 14 works as a chip discharging channel for expelling upper gum chips or excessive bone growth powder/biomedical filler. This embodiment is practical for a patient who needs a smaller amount of bone growth powder/biomedical filler to be filled in the sinus floor.

Figure 10:
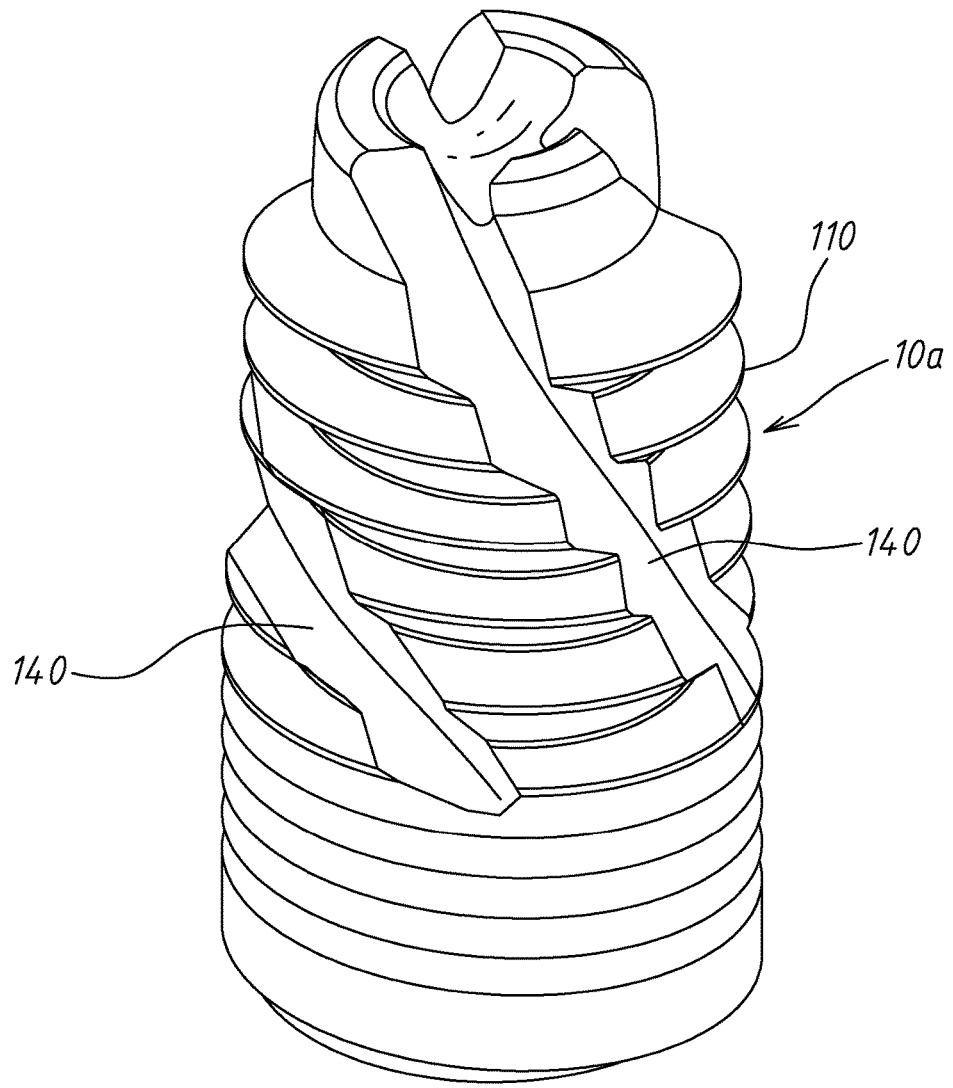
FIG. 10 is an oblique top elevational view of a sinus implant in accordance with a second embodiment of the present invention.
Figure 11:
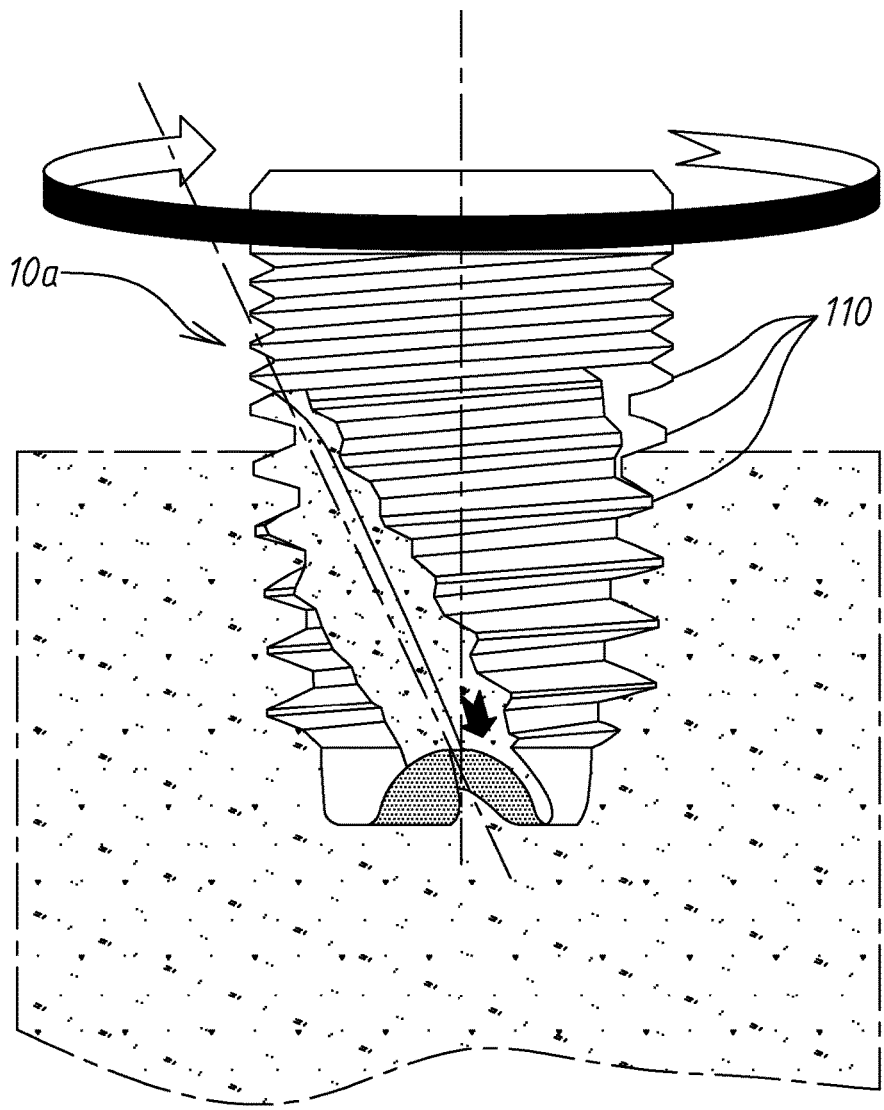
FIG. 11 is a schematic drawing illustrating the action of the installation of the sinus implant of the second embodiment of the present invention in the upper gum.

FIG. 10 illustrates a sinus implant 10a in accordance with a second embodiment of the present invention. This second embodiment is substantially similar to the aforesaid first embodiment with the exception that the spiral grooves 140 and positioning threads 110 of the sinus implant 10a of this second embodiment extend spirally in reversed directions, i.e., the positioning threads 110 extend spirally and upwardly in a clockwise direction, and the spiral grooves 140 extend spirally and downwardly in a counter-clockwise direction. Thus, when driving the sinus implant 10a into the patient's upper gum in a clockwise direction, as shown in FIG. 11, the bone growth powder/biomedical filler and cut chips will be wholly forced by the positioning threads 110 into the crevice between the sinus floor and the upper gum. Thus, this embodiment is practical for a patient who needs a large amount of bone growth powder/biomedical filler to be filled in the sinus floor.

In conclusion, the invention provides a sinus implant that is not only effective to prevent piercing the sinus floor in the sinus implant surgery but also capable of synchronously pushing a selected amount of bone growth powder/biomedical filler into the sinus floor when it is driven into position.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A sinus implant, comprising:
an implant body having a mounting hole axially defined there through;
a plurality of positioning threads that are provided in a periphery of the implant body, that extend spirally upwardly around the periphery of the implant body, and that have a width that gradually decreases in a direction from a bottom end of the implant body toward an opposing top end of the implant body;
a pushing portion that protrudes from a top end of the sinus implant, that has a diameter that is reduced compared to that of the implant body, and that comprises a flat end face having defined therein a recess space and that includes an outer guide edge that is a smoothly arched and extends around a border of the flat end face, and an inner guide edge that is a smoothly arched and extends around the recess space within the flat end face, wherein, the pushing portion has a periphery that is without the plurality of positioning threads; and
at least one spiral groove that extends around the periphery of the implant body across the plurality of positioning threads, that reaches the periphery of the pushing portion, and that intersects with and communicates with the recess space.

2. The sinus implant as claimed in claim 1, wherein the recess space has a shape of a hemisphere.

3. The sinus implant as claimed in claim 1, wherein the plurality of positioning threads and each spiral groove of the at least one spiral groove extends spirally in respective directions that are reversed to one another.

4. A method of implanting a sinus implant in the vicinity of a sinus cavity, comprising:
providing a sinus implant according to claim 1; and
pushing the sinus implant through an upper gum without damaging or piercing a floor of the sinus cavity.

5. The method according to claim 4, wherein the sinus implant accommodates, in the mounting hole axially defined in the implant body, a filler comprised of bone growth filler and biomedical filler, and wherein pushing the sinus implant through the upper gum synchronously pushes the filler from the sinus implant into a crevice created during pushing between the upper gum and the floor of the sinus cavity.

6. A sinus implant, comprising:
an implant body having a mounting hole axially defined therein;
a plurality of positioning threads that are provided in a periphery of the implant body, that extend spirally upwardly, and that have a width that gradually reduces in a direction from a bottom side of the implant body toward an opposing top side of the implant body;
at least one spiral groove extending around the periphery of the implant body across the plurality of positioning threads; and
a pushing portion that has a diameter that is reduced compared to that of the implant body, that is located at a top end of the sinus implant, that includes a flat end face in which is defined a recess space that is in communication with each spiral groove of the at least one spiral groove; and that includes an outer guide edge that is smoothly arched and that extends around a border of the flat end face; and an inner guide edge that is smoothly arched and that extends around the recess space within the flat end face,
wherein the pushing portion has a periphery that is without the plurality of positioning threads, and
wherein the plurality of positioning threads and each spiral groove of the at least one spiral groove extends spirally in respective directions that are reversed to one another.

7. The sinus implant as claimed in claim 6, wherein the recess space has a shape of a hemisphere.

8. A method of implanting a sinus implant in the vicinity of a sinus cavity, comprising:
providing a sinus implant according to claim 6; and
pushing the sinus implant through an upper gum without damaging or piercing a floor of the sinus cavity.

9. The method according to claim 8, wherein the sinus implant accommodates, in the mounting hole axially defined in the implant body, a filler comprised of bone growth filler and biomedical filler, and wherein pushing the sinus implant through the upper gum synchronously pushes the filler from the sinus implant into a crevice created during pushing between the upper gum and the floor of the sinus cavity.

* * * * *